United States Patent

Nakagami

[19]

[11] Patent Number: 5,928,199
[45] Date of Patent: Jul. 27, 1999

[54] WINGED NEEDLE ASSEMBLY

[75] Inventor: Hiroyuki Nakagami, Osaka, Japan

[73] Assignee: Nissho Corporation, Osaka, Japan

[21] Appl. No.: 08/934,755

[22] Filed: Sep. 22, 1997

[30] Foreign Application Priority Data

Sep. 20, 1996 [JP] Japan ................................ 8-249773

[51] Int. Cl.$^6$ ................................................ A61M 5/00
[52] U.S. Cl. ............................................ 604/171; 604/177
[58] Field of Search .................................. 604/171, 177, 604/192, 198, 240, 263, 158, 165

[56] References Cited

U.S. PATENT DOCUMENTS

| 4,362,156 | 12/1982 | Feller, Jr. et al. . |
| 4,840,613 | 6/1989 | Balbierz . |
| 4,923,445 | 5/1990 | Ryan . |
| 5,085,639 | 2/1992 | Ryan . |

FOREIGN PATENT DOCUMENTS 0 664 139A1   7/1995   European Pat. Off. .

WO 92/11885   7/1992   WIPO .

*Primary Examiner*—Ronald Stright
*Assistant Examiner*—A. T. Nguyen
*Attorney, Agent, or Firm*—Kubovcik & Kubovcik

[57] ABSTRACT

A winged needle assembly including a cannula 1, a hub 2, a tube 3 and a cylindrical holder 4 provided with wings at the distal end thereof and retaining the hub therein. The hub 2 is slidable along the inner wall of the cylindrical holder 4 from a first position near the distal end of the cylindrical holder 4 up to a second position near the proximal end thereof. Further, between the hub 2 and the cylindrical holder 4, there are provided a first locking arrangement (21,41) for releasably locking the hub 2 at the first position of the cylindrical holder 4 and a second locking arrangement (22,42,23,43) for substantially unreleasably locking the hub 2 at the second position of the cylindrical holder 4. With the above structure, the edge of the needle can be smoothly retracted and protected within the cylindrical holder without any sense of frictional resistance to medical personnel using the needle while the wings are kept fixed to the skin of a patient.

4 Claims, 5 Drawing Sheets

WINGED NEEDLE ASSEMBLY

BACKGROUND OF THE INVENTION

1. Field of the Invention

The present invention relates to a winged needle assembly and, more particularly, to a winged needle assembly having a winged cylindrical holder for preventing sticking accidents taking place when restoring the needle into a protector and which can protect the edge of the needle by merely sliding the needle along the inner wall of the winged cylindrical holder.

2. Description of the Prior Art

Conventionally, medical needles have usually been made separable from protectors in which they are accommodated. When used needles have been restored into the protectors, the fingers of operators often have been accidentally stuck by the edges (or tips) of the needles. As a result, there has been a possibility that medical personnel using such needles might be infected with AIDS or hepatitis. Therefore, in order to prevent such sticking accidents various proposals have been made. One of such proposals is a winged needle assembly disclosed in U.S. Pat. No. 5,120,320 wherein a protector having a pair of slits is integrally attached to the winged needle. In this assembly a used needle is allowed to slide backward along the slits of the protector to protect the edge of the used needle within the protector.

Another example is an injection needle assembly disclosed in Japanese Unexamined Patent Publication No. H-1-212561 wherein the injection needle assembly comprises an injection needle and a winged protector. In this assembly a required position regulating means is provided between the needle and the protector so that the edge of the needle can be protected within the protector by sliding the protector toward the distal end of the needle.

However, the winged needle assembly disclosed in above-mentioned U.S. Pat. No. 5,120,320 has the disadvantage that the needle can not be retracted into the protector while indwelling, since the wings fixed to the needle are secured to the skin of a patient by means of a tape or the like. Therefore, it is necessary for the needle to slide and be accommodated in the protector after removing the tape and drawing out the needle from the patient's skin.

The injection needle assembly disclosed in above-mentioned Japanese Unexamined Patent Publication No. H-1-212561 has the following problems due to its structural defects. When the needle is stuck into a patient's skin, the needle body moves backward due to the penetration force. The needle body tends to slip off the protector when it is pulled backward to retract the needle edge into the winged protector. Since the hub of the needle and the protector are to be firmly fitted with each other at a required position, the resistance in releasing the engagement of the two members after use or in sliding the hub along the inner wall of the protector is so large that the physical burden on medical personnel handling the needle assembly increases and the patient is given a sense of uneasiness.

In order to solve the above-described problems, the present applicant proposed in Japanese Unexamined Patent Publication No. H-7-5671 a winged needle assembly comprising a needle, a winged cylindrical holder for retaining the needle therein for protection and a hub which is movable from a first position at which the edge of the needle projects from the cylindrical holder by a predetermined length to a second position at which the edge of the needle is received within the cylindrical holder, and wherein interlocking means is provided between the hub and the cylindrical holder. In this assembly, at the first position at which the needle edge is exposed from the cylindrical holder by a predetermined length, the movement of the hub toward the second position at which the needle edge is received in the holder is prevented. While, after the hub has been slid to the second position, the movement of the hub toward the first position is prevented. However, this arrangement has not always satisfied medical personnel or patients using the winged needle assembly because when the interlocking means is released at the first position and the hub is moved toward the second position, there is some degree of frictional resistance.

SUMMARY OF THE INVENTION

The present invention has been developed in view of the above-described situation. An object of the present invention is to provide a winged needle assembly capable of protecting the edge of an injection needle within a winged cylindrical holder by merely sliding the needle along the inner wall of the cylindrical holder. Another object of the invention is to provide a winged needle assembly which is capable of protecting the edge of the injection needle by smoothly restoring the needle within the winged cylindrical holder without giving any sense of frictional resistance to medical personnel while the wings of the cylindrical holder are kept fixed to the skin of a patient.

To achieve the above-described objects of the present invention, the winged needle assembly comprises a cannula having an edge at a distal end thereof, a hub having a distal end and a proximal end and supporting the proximal end of the cannula with the distal end thereof, a tube connected to the proximal end of the hub, and a cylindrical holder for retaining the hub therein and having a distal end and a proximal end and being provided with a pair of flexible wings on the outer peripheral wall of the distal end thereof. The hub can smoothly slide along the inner wall of the cylindrical holder from a first position at which the distal end of the cannula supported by the hub projects beyond the distal end of the cylindrical holder by a predetermined length to a second position at which the distal end of the cannula is received within the cylindrical holder. Additionally, between the hub and the cylindrical holder, there is provided a locking mechanism comprising a first locking means for releasably locking the hub at the first position of the cylindrical holder and a second locking means for substantially unreleasably locking the hub at the second position of the cylindrical holder.

In the above arrangement, it is preferable that the first locking means includes a locked portion provided at the proximal end of the hub and a locking portion provided at the proximal end of the cylindrical holder. In that case, the locked portion may include a pair of hooked flexible locking arms extending from the proximal end to the distal end of the locked portion, while the locking portion may have a pair of locking holes at the proximal end thereof, whereby when the hub is at the first position of the cylindrical holder, the hooked locking arms are engaged with the locking holes, respectively. Alternatively, the locked portion may have a pair of holed flexible locking arms extending from the proximal to the distal end thereof, while the locking portion may have a pair of locking projections, whereby when the hub is at the first position of the cylindrical holder, the locking projections of the locking portion are engaged with the holes of the locking arms of the locked portion, respectively.

Further, it is preferable that the second locking means comprises a locked portion provided at the distal end of the hub and a locking portion provided at the proximal end of the cylindrical holder. In that case, it is preferable that the locked portion comprises an annular projection provided at the distal end of the hub and an annular groove formed over a predetermined length from the annular projection toward the proximal end of the hub, while the locking portion comprises a flange provided near the distal end of the locking portion in proximity to the locking holes in the inner wall of the cylindrical holder and a flexible abutment branch having a length equal to the width of the annular groove and extending from the flange toward the proximal end of the cylindrical holder. When the hub is at the second position of the cylindrical holder, an end surface of the annular projection on the annular groove side of the hub abuts against the flange and the end surface of the annular groove on the side of the proximal end of the hub abuts against the distal end of the flexible abutment branch.

DESCRIPTION OF PREFERRED EMBODIMENT

Figure 1:
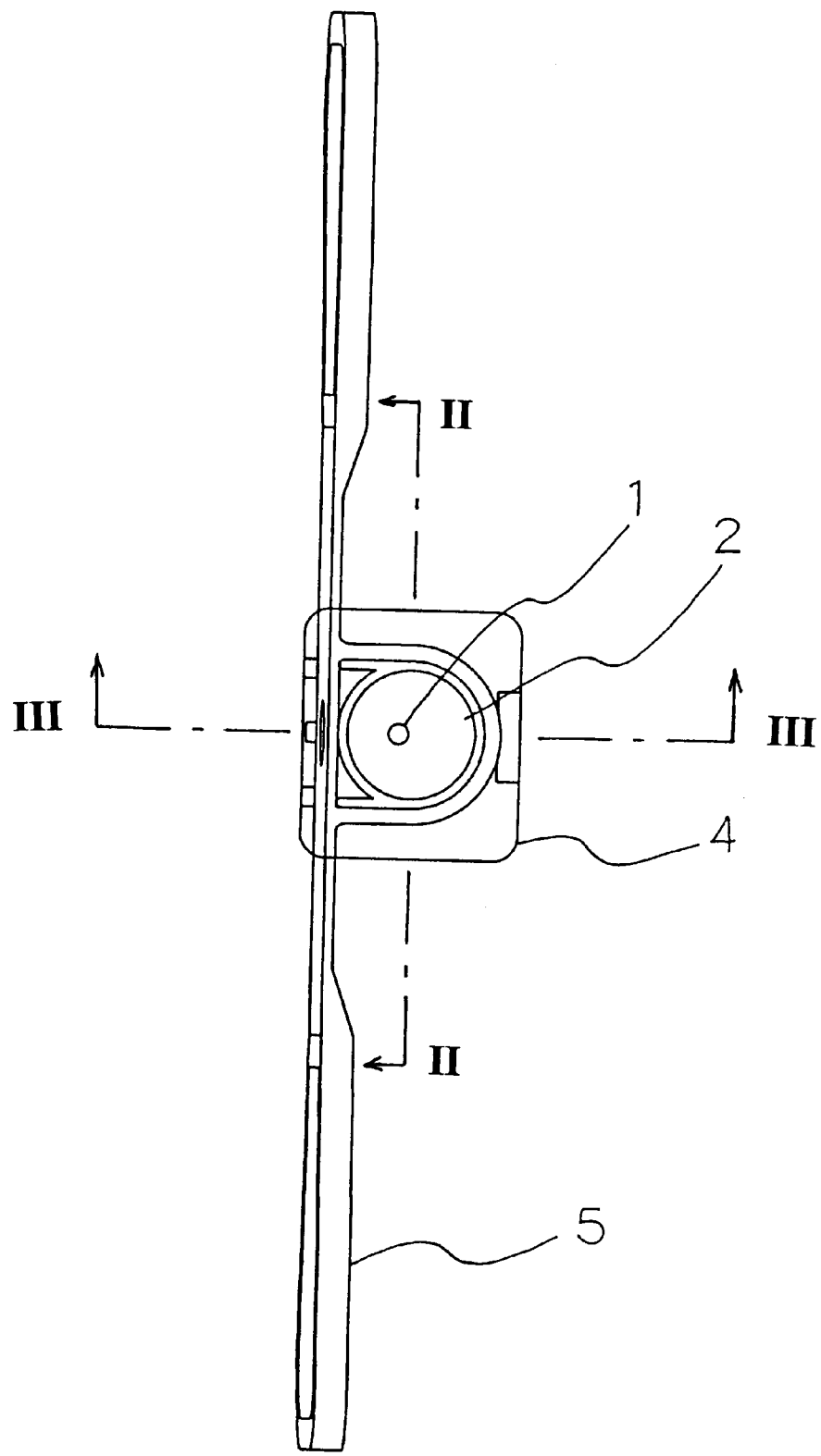
FIG. 1 is a front view of a winged needle assembly according to the present invention.

A preferred embodiment of the present invention will be described with reference to the accompanying drawings.

As shown in FIGS. 1 through 5, the winged needle assembly according to the present invention comprises a cannula 1, a hub 2 supporting the proximal end of the cannula 1, a tube 3 connected to a proximal end of the hub 2 and a cylindrical holder 4 retaining the hub 2 therein. The cylindrical holder 4 is provided with wings 5 at the distal end thereof. The hub 2 is capable of sliding smoothly along the inner wall of the cylindrical holder 4 from a first position near the distal end of the cylindrical holder 4 to a second position near the proximal end of the cylindrical holder 4. Between the hub 2 and the cylindrical holder 4, there is provided a locking mechanism which comprises first locking means (21, 41) for releasably locking the hub 2 at the first position of the cylindrical holder 4 and second locking means (22, 42, 23, 43) for substantially unreleasably locking the hub 2 at the second position of the cylindrical holder 4.

The cannula 1 is a hollow needle made of a metal such as stainless steel (typically SUS304) and has an edge 11 at the distal end thereof. The proximal end of the cannula is supported by the distal end of the hub 2. The hub 2 is usually made of a flexible resin material such as polypropylene, polyester, polyethylene, etc. The outer wall of the distal end of the hub 2 has an annular projection 22 and an annular groove 23 extending from the annular projection 22 toward the proximal end of the hub 2. At the proximal end of the hub 2 there are provided a connecting portion 24 for the tube 3 and a pair of flexible locking arms 21 extending from the connecting portion 24 toward the distal end of the hub 2. As each of the pair of locking arms 21, there is employed an arm having a hook 211 at the distal end and capable of flexing in the direction of the axis of the hub 2 by means of a slit 212 as shown in FIGS. 2 through 5. The pair of locking arms 21 may be formed integral with the hub 2 or may be formed separately from the hub 2 so as to be attached thereto later.

Figure 2:
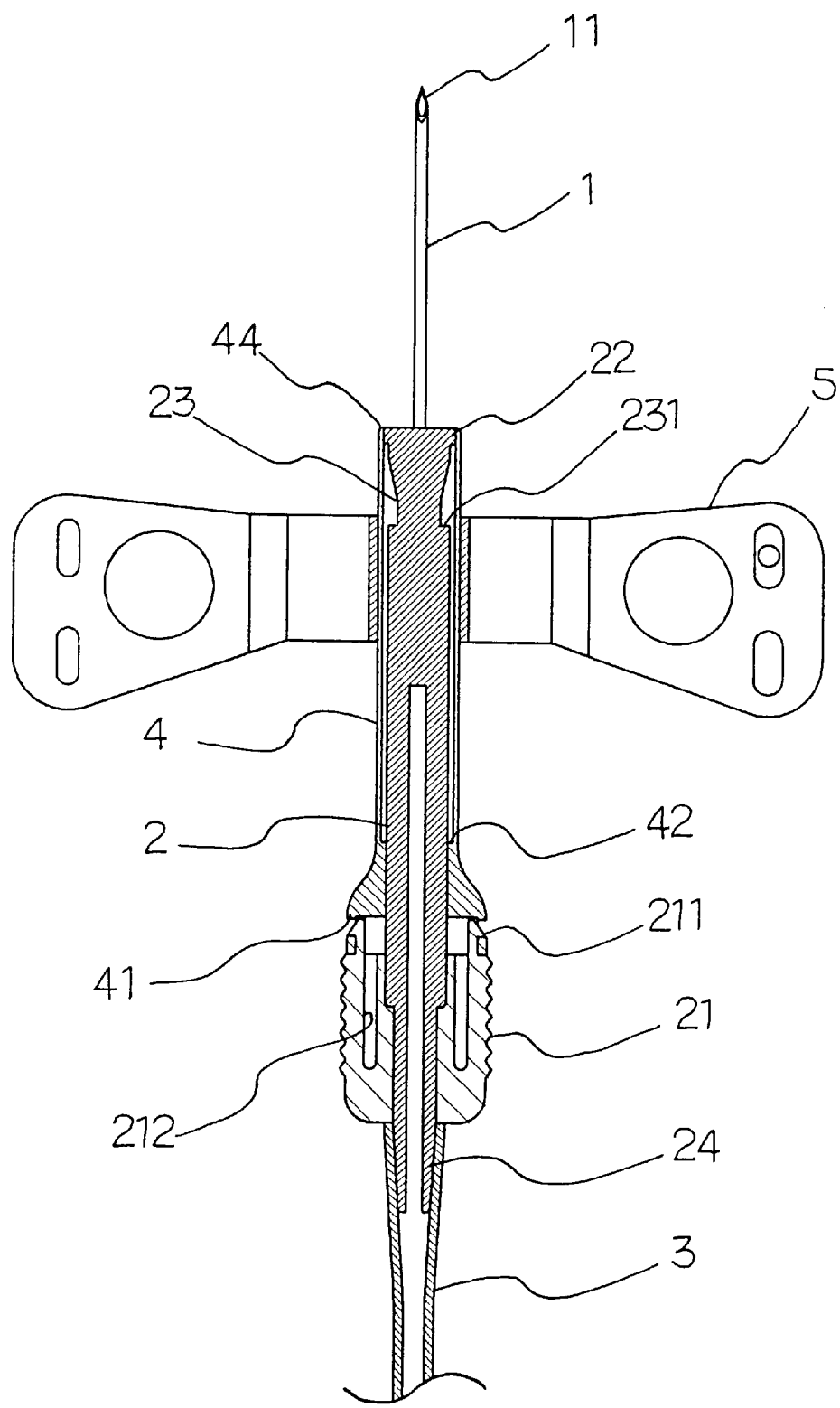
FIG. 2 is a cross sectional view taken along line II—II of FIG. 1.
Figure 4:
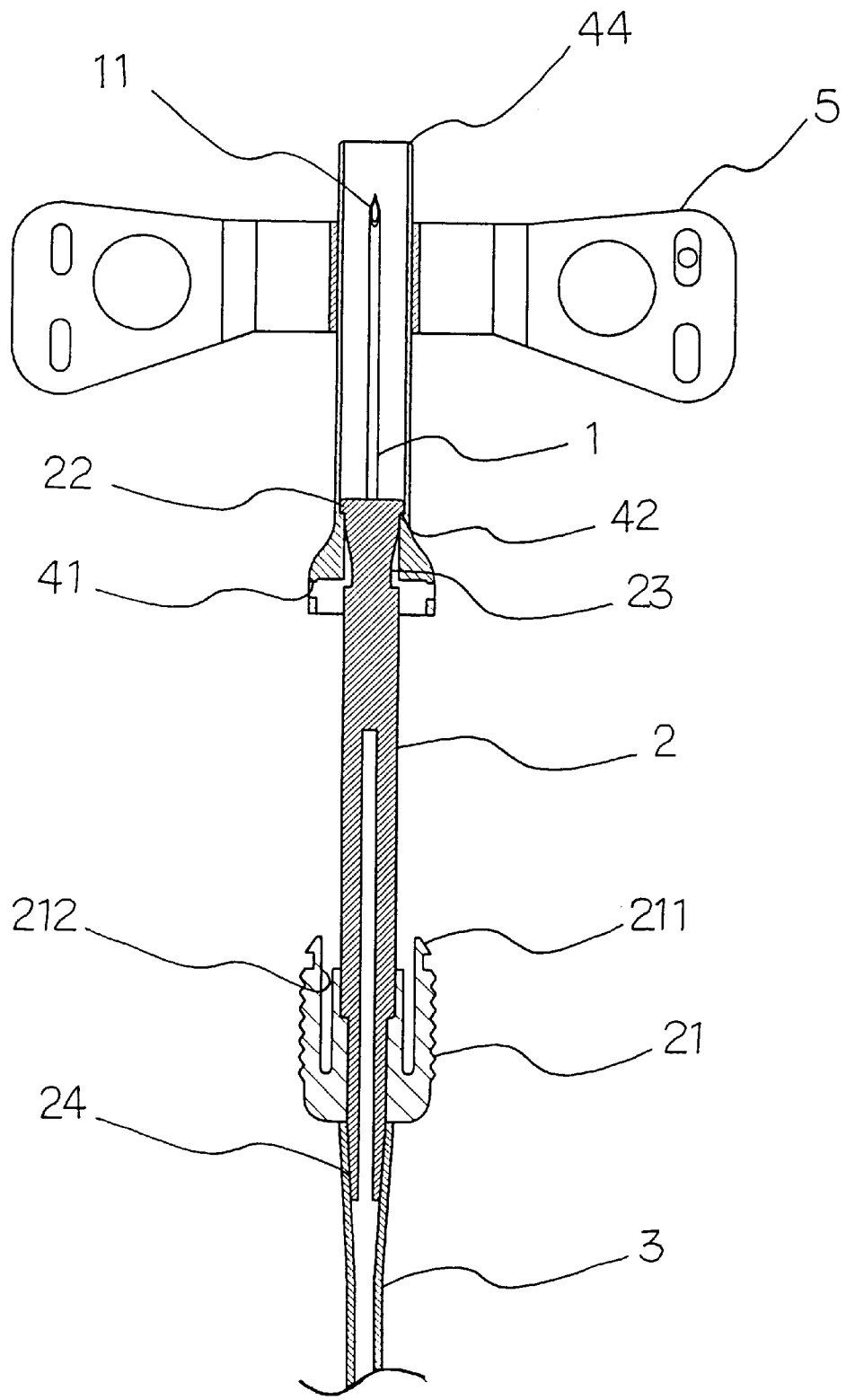
FIG. 4 is a cross sectional view taken along line II—II of FIG. 1 when the injection needle is in a state in which the tip of the injection needle is retained within the cylindrical holder as a result of sliding the hub backward.

The cylindrical holder 4 is a cylindrical member for holding the hub 2 therein and is provided with a pair of flexible wings 5 on the outer peripheral wall of the distal end thereof. The hub 2 is slidable along the inner wall of the cylindrical holder 4 from a first position at which the cannula 1 projects from a distal end 44 of the cylindrical holder 4 by a predetermined length up to a second position at which the distal end of the cannula 1 is received within the cylindrical holder 4. Locking holes 41 are provided at the inner wall of the proximal end of the cylindrical holder 4, as shown in FIGS. 2 and 4.

The first locking means is comprised of the locking holes 41 as a locking portion and the locking arms 21 of the hub 2 as a locked portion. Thus, by fitting the hooks 211 of the locking arms 21 of the hub 2 into the locking holes 41, respectively, the holes 41 and the hooks 211 are releasably brought into engagement with each other, respectively. To release the locking mechanism, the locking arms 21 may be flexed inward, i.e., in the direction of axis of the hub 2, to withdraw the hooks 211 from the holes 41 and then are pulled backward, i.e., toward the tube 3.

On the inner wall of the cylindrical holder 4, there is provided a flange 42 facing the distal end of the cylindrical holder 4 in the proximity of the locking holes 41. This flange 42 has a flexible abutment branch 43 extending toward the proximal end of the cylindrical holder 4. The flexible abutment branch 43 has a length equal to about the width of the annular groove 23 of the hub 2.

The second locking means is comprised of the flexible abutment branch 43 and the flange 42 of the cylindrical holder 4 as a locking portion and the annular projection 22 and the annular groove 23 of the hub 2 as a locked portion. Thus, due to the provision of the second locking means, when the hub 2 is at the second position of the cylindrical holder 4, the end surface of the annular projection 22 of the hub 2 on the annular groove side abuts against the flange 42 thereby preventing the backward movement of the hub 2 and at the same time, an end surface 231 of the annular groove 23 on the proximal end side of the hub 2 abuts against the distal end of the flexible abutment branch 43 thereby preventing the forward movement of the hub 2. By this structure the hub 2 is substantially unreleasably locked at the second position of the cylindrical holder 4.

Figure 3:
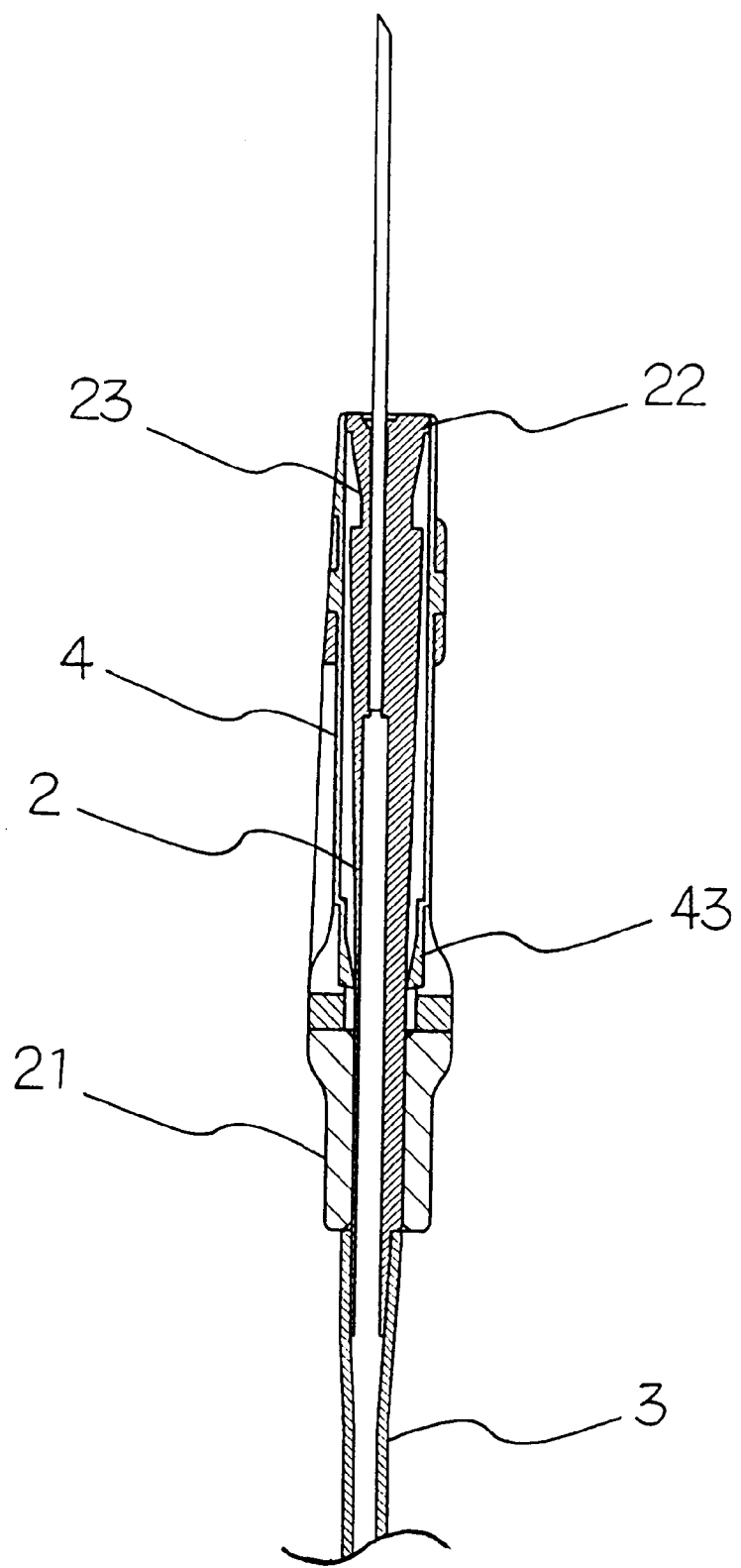
FIG. 3 is a cross sectional view taken along line III—III of FIG. 1.

When the winged needle assembly is in use, the positional relationship between the hub 2 and the cylindrical holder 4 is as shown in FIGS. 2 and 3. In this state, the hub 2 is at the first position of the cylindrical holder 4 and accordingly, the edge 11 at the distal end of the cannula 1 projects beyond the distal end 44 of the cylindrical holder 4 by a predetermined length. In the first position of the cylindrical holder 4, the hub 2 and the cylindrical holder 4 are held in engagement with each other by the first locking means comprising the locking arms 21 of the hub 2 (more accurately, the hooks 211 of the locking arms 21) and the locking holes 41 of the cylindrical holder 4. Thus, when the winged needle assembly is stuck to the skin of a patient, the hub 2 is prevented from moving backward, i.e., toward the proximal end of the cylindrical holder 4.

Figure 5:
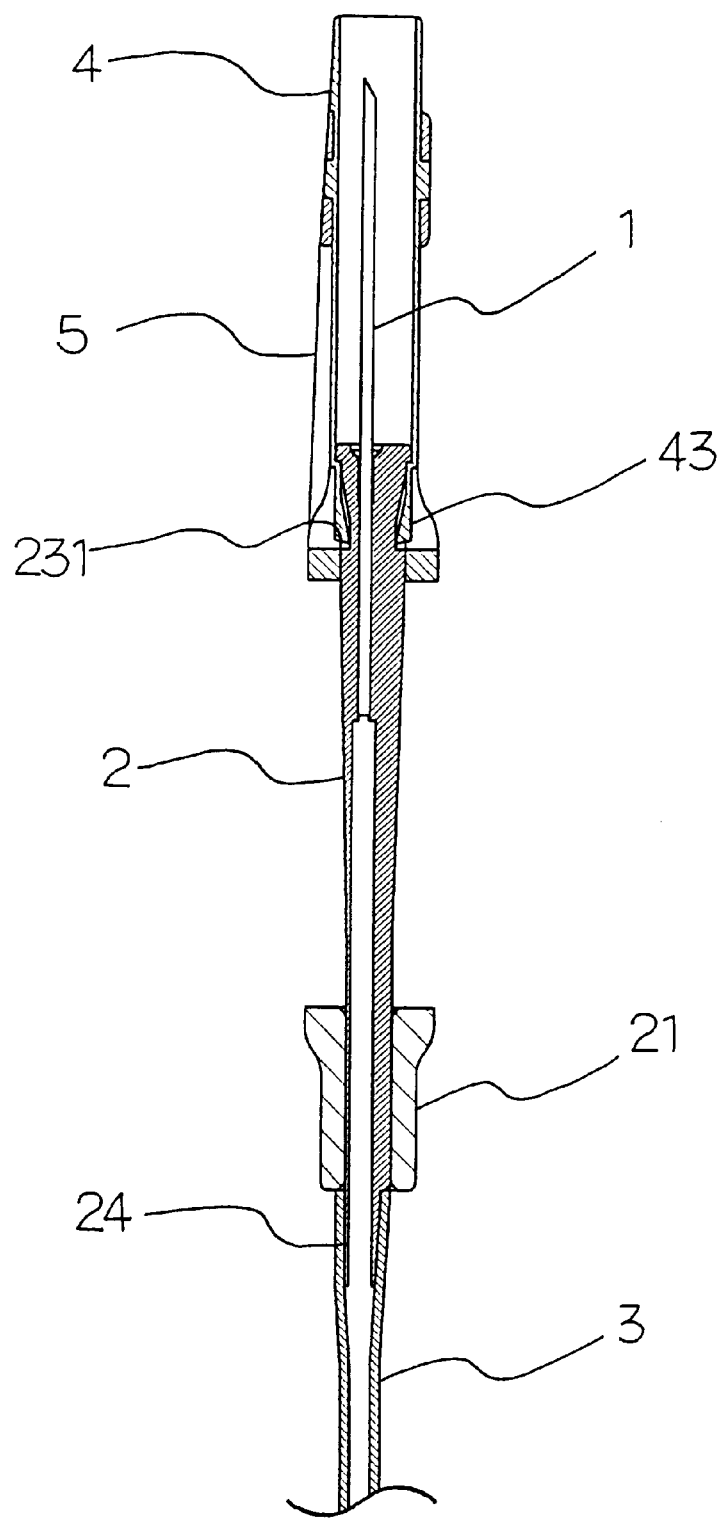
FIG. 5 is a cross sectional view taken along line III—III of FIG. 1 when the injection needle is in a state in which the tip of the injection needle is retained within the cylindrical holder as a result of sliding the hub backward.

The state of the winged needle assembly after use is as shown in FIGS. 4 and 5. When the user grips the locking arms 21 with his or her fingers, the locking arms 21 flex inward to become disengaged from the locking holes 41. Then, when the hub 2 is moved backward while the user keeps gripping the locking arms 21 with his fingers, the annular projection 22 of the hub 2 will be brought into contact with the flange 42 of the cylindrical holder 4 at the second position of the cylindrical holder 4. Thereby, the hub 2 is prevented from moving backward. At the same time, end surface 231 of the annular groove 23 on the proximal end side of the hub 2 and the tip of the flexible abutment branch 43 abut against each other. Thereby the hub is prevented from moving forward (see FIGS. 4 and 5). In this case, the edge 11 of the cannula 1 is completely received in the cylindrical holder 4.

As will be clear from the foregoing description, the winged needle assembly according to the present invention has the following various advantages. A possible sticking accident of medical personnel can be securely prevented. The winged needle assembly can be handled more easily than the type of assembly having removable wings, since the edge of the injection needle can be accommodated in the cylindrical holder by merely moving the hub along the inner wall of the cylindrical holder toward the proximal end of the cylindrical holder. The physical burden of medical personnel is minimized thereby mitigating the sense of uneasiness of a patient, since the hub can be unlocked smoothly from the cylindrical holder after using the winged needle assembly and can be slid smoothly along the inner wall of the cylindrical holder almost without any resistance.

What is claimed is:

1. A winged needle assembly comprising a cannula having an edge at a distal end thereof; a hub having a distal end and a proximal end and supporting a proximal end of the cannula in the distal end thereof; a tube connected to the proximal end of the hub; a cylindrical holder for retaining the hub therein and having a distal end and a proximal end, said hub being slidable along the inner wall of said cylindrical holder from a first position at which the distal end of said cannula supported by said hub projects beyond the distal end of said cylindrical holder by a predetermined length to a second position at which said distal end of the cannula is received within said cylindrical holder; a pair of flexible wings provided on the outer peripheral wall of the distal end of said cylindrical holder; and first and second locking means provided between said hub and said cylindrical holder such that said first locking means releasably locks said hub at said first position of the cylindrical holder and said second locking means substantially unreleasably locks said hub at said second position of the cylindrical holders; said second locking means comprising a locked portion provided at the distal end of said hub and a locking portion provided at the proximal end of said cylindrical holder, said locked portion comprising an annular projection provided at the distal end of said hub and an annular groove formed over a predetermined length from said annular projection in the direction of the proximal end of said hub and said locking portion comprising a flange provided on a distal end side thereof and a flexible abutment branch having a length equal to the width of said annular groove and extending from said flange toward the proximal end of said cylindrical holder, whereby when said hub is at the second position of said cylindrical holder an end surface of said annular projection on the annular groove side thereof abuts against said flange and an end surface of said annular groove abuts against the distal end of said flexible abutment branch.

2. A winged needle assembly according to claim 1, wherein said first locking means comprises a locked portion provided at the proximal end of said hub and a locking portion provided at the proximal end of said cylindrical holder.

3. A winged needle assembly according to claim 2, wherein said locked portion includes a pair of flexible locking arms with hooks and extending from a proximal end of said locked portion toward a distal end of said locked portion and said locking portion has a pair of locking holes at a proximal end thereof, whereby when said hub is at the first position of said cylindrical holder, the hooks of said locking arms engage with said pair of locking holes, respectively.

4. A winged needle assembly according to claim 2, wherein said locked portion has a pair of flexible locking arms extending from a proximal end of said locked portion toward a distal end of said locked portion, each arm having a hole at a distal end thereof; and wherein said locking portion has a pair of locking projections at the proximal end thereof, whereby when said hub is at the first position of said cylindrical holder, the holes of said locking arms engage with said locking projections.

* * * * *